(12) United States Patent
Lee et al.

(10) Patent No.: US 12,133,988 B2
(45) Date of Patent: Nov. 5, 2024

(54) IMPLANTABLE APPARATUS

(71) Applicants: Samsung Electronics Co., Ltd., Suwon-si (KR); POSTECH Research and Business Development Foundation, Pohang-si (KR)

(72) Inventors: Jaechun Lee, Seoul (KR); Sang Joon Kim, Hwaseong-si (KR); Won Ok Kang, Pohang-si (KR); Jonghan Kim, Seoul (KR); Jun Seung Mun, Pohang-si (KR); Sung Min Park, Seoul (KR); Chisung Bae, Yongin-si (KR)

(73) Assignees: Samsung Electronics Co., Ltd., Suwon-si (KR); POSTECH Research and Business Development Foundation, Pohang-si (KR)

( * ) Notice: Subject to any disclaimer, the term of this patent is extended or adjusted under 35 U.S.C. 154(b) by 317 days.

(21) Appl. No.: 17/190,594

(22) Filed: Mar. 3, 2021

(65) Prior Publication Data

US 2022/0072318 A1 Mar. 10, 2022

(30) Foreign Application Priority Data

Sep. 7, 2020 (KR) ........................ 10-2020-0114049

(51) Int. Cl.
*A61N 1/378* (2006.01)
*A61B 5/00* (2006.01)
*A61N 1/372* (2006.01)
*H02J 50/00* (2016.01)

(52) U.S. Cl.
CPC .......... *A61N 1/3787* (2013.01); *A61B 5/6847* (2013.01); *A61N 1/37229* (2013.01); *H02J 50/005* (2020.01); *A61B 2560/0219* (2013.01)

(58) Field of Classification Search
CPC .............. A61N 1/3787; A61N 1/37229; A61B 5/6847; H02J 50/005
See application file for complete search history.

(56) References Cited

U.S. PATENT DOCUMENTS

| 8,581,542 | B2 | 11/2013 | Cook et al. | |
|---|---|---|---|---|
| 8,797,225 | B2 | 8/2014 | Kato | |
| 2009/0270948 | A1* | 10/2009 | Nghiem | A61N 1/37229 607/60 |
| 2019/0143126 | A1* | 5/2019 | Wheeler | A61N 1/37211 607/60 |

(Continued)

FOREIGN PATENT DOCUMENTS

| JP | 5630566 B2 | 11/2014 |
|---|---|---|
| KR | 10-2010-0067676 A | 6/2010 |

(Continued)

*Primary Examiner* — Tammie K Marlen
(74) *Attorney, Agent, or Firm* — NSIP Law

(57) ABSTRACT

Implantable apparatuses are provided, where the implantable apparatus includes a first electrode, a second electrode, an electrode signal transceiver connected to the first electrode and the second electrode, an antenna, a wireless power receiver connected to the antenna, and a conductor case configured to protect the electrode signal transceiver and the wireless power receiver. The antenna be spaced apart from the conductor case and encloses the conductor case, and a plane in which the antenna is disposed is at a same level or at a higher level than a top surface of the conductor case.

21 Claims, 9 Drawing Sheets

(56) References Cited

U.S. PATENT DOCUMENTS

2020/0001094 A1    1/2020  Lyer et al.

FOREIGN PATENT DOCUMENTS

| KR | 10-1126606 B1 | 3/2012 |
| KR | 10-1671461 B1 | 11/2016 |
| KR | 10-1686633 B1 | 12/2016 |
| KR | 10-2007824 B1 | 8/2019 |

* cited by examiner

IMPLANTABLE APPARATUS

CROSS-REFERENCE TO RELATED APPLICATIONS

This application claims the benefit under 35 USC § 119(a) of Korean Patent Application No. 10-2020-0114049, filed on Sep. 7, 2020, in the Korean Intellectual Property Office, the entire disclosure of which is incorporated herein by reference for all purposes.

BACKGROUND

Field

The following description relates to wireless power reception and object stimulation technology, and more particularly, to technology of sharing electrodes in wirelessly transmitting power or transmitting and receiving electrode signals.

2. Description of Related Art

An implantable device is inserted into a human body and is used to sense biometric information or used for treatment. Since the implantable device needs to be inserted into the human body, a volume of the implantable device needs to be small. Since it is difficult to attach or detach the implantable device, power is wirelessly supplied to the implantable device from outside the body, instead of replacing a battery. To apply a stimulation signal to a human body while wirelessly receiving power supply in a state in which the implantable device is inserted into the human body, a wireless power reception device requires an electrode for electrical stimulation and a coil for wirelessly receiving power.

The inventors have derived the above description in the course of conceiving the present disclosure and is not necessarily a publicly known before the filing of the present application.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an implantable apparatus including a first electrode, a second electrode, an electrode signal transceiver connected to the first electrode and the second electrode, an antenna, a wireless power receiver connected to the antenna, and a conductor case configured to protect the electrode signal transceiver and the wireless power receiver, wherein the antenna is spaced apart from the conductor case and encloses the conductor case, and a plane in which the antenna is disposed is at a same level or at a higher level than a top surface of the conductor case.

The implantable apparatus may include ferrite disposed between the conductor case and the antenna.

The antenna may be connected via a feed-through to the wireless power receiver, and the antenna may be electrically insulated from the conductor case.

The feed-through may include a conductive wire covered with an insulator.

The insulator may be fastened in a hole, and the conductive wire may be connected to the antenna and a circuit in the conductor case.

The implantable apparatus may include an insulator case configured to protect the first electrode, the second electrode, the antenna, and the conductor case, wherein the insulator case may be configured to fix the first electrode, the second electrode and a protruding portion of the conductor case.

In another general aspect, there is provided an implantable apparatus including a first electrode, a second electrode, an electrode signal transceiver connected to the first electrode and the second electrode, an antenna, a wireless power receiver connected to the antenna, and a conductor case configured to protect the electrode signal transceiver and the wireless power receiver, wherein the antenna is configured to enclose the conductor case, the first electrode and the second electrode, and the first electrode and the second electrode do not protrude outward from the antenna.

The implantable apparatus may include ferrite disposed between the conductor case and the antenna.

The antenna may be connected via a feed-through to the wireless power receiver, and the antenna may be electrically insulated from the conductor case.

The implantable apparatus may include an insulator case configured to protect the first electrode, the second electrode, the antenna, and the conductor case, wherein the insulator case may be configured to fix the first electrode, the second electrode and a protruding portion of the conductor case.

In another general aspect, there is provided an implantable apparatus including a first electrode, a second electrode, an electrode signal transceiver connected to the first electrode and the second electrode, an antenna, a wireless power receiver connected to the antenna, and a conductor case configured to protect the electrode signal transceiver and the wireless power receiver, wherein the antenna is configured to enclose the conductor case, a portion of the antenna is disposed above each of the first electrode and the second electrode, and a height of the antenna is greater than or equal to a threshold.

The implantable apparatus may include ferrite disposed between the conductor case and the antenna.

The antenna may be connected via a feed-through to the wireless power receiver, and the antenna may be electrically insulated from the conductor case.

The implantable apparatus may include an insulator case configured to protect the first electrode, the second electrode, the antenna, and the conductor case, wherein the insulator case may be configured to fix the first electrode, the second electrode and a protruding portion of the conductor case.

In another general aspect, there is provided an implantable apparatus including a first electrode, a second electrode, an electrode signal transceiver connected to the first electrode and the second electrode, an antenna, a wireless power receiver connected to the antenna, and a conductor case configured to protect the electrode signal transceiver and the wireless power receiver, wherein the antenna encloses the conductor case and is disposed at a higher level than each of the first electrode and the second electrode, and the first electrode and the second electrode protrude outward from the antenna.

The implantable apparatus may include ferrite disposed between the conductor case and the antenna.

The antenna may be connected via a feed-through to the wireless power receiver, and the antenna may be electrically insulated from the conductor case.

The implantable apparatus may include an insulator case configured to protect the first electrode, the second electrode, the antenna, and the conductor case, wherein the insulator case may be configured to fix the first electrode, the second electrode and a protruding portion of the conductor case.

Other features and aspects will be apparent from the following detailed description, the drawings, and the claims.

Figure 1:
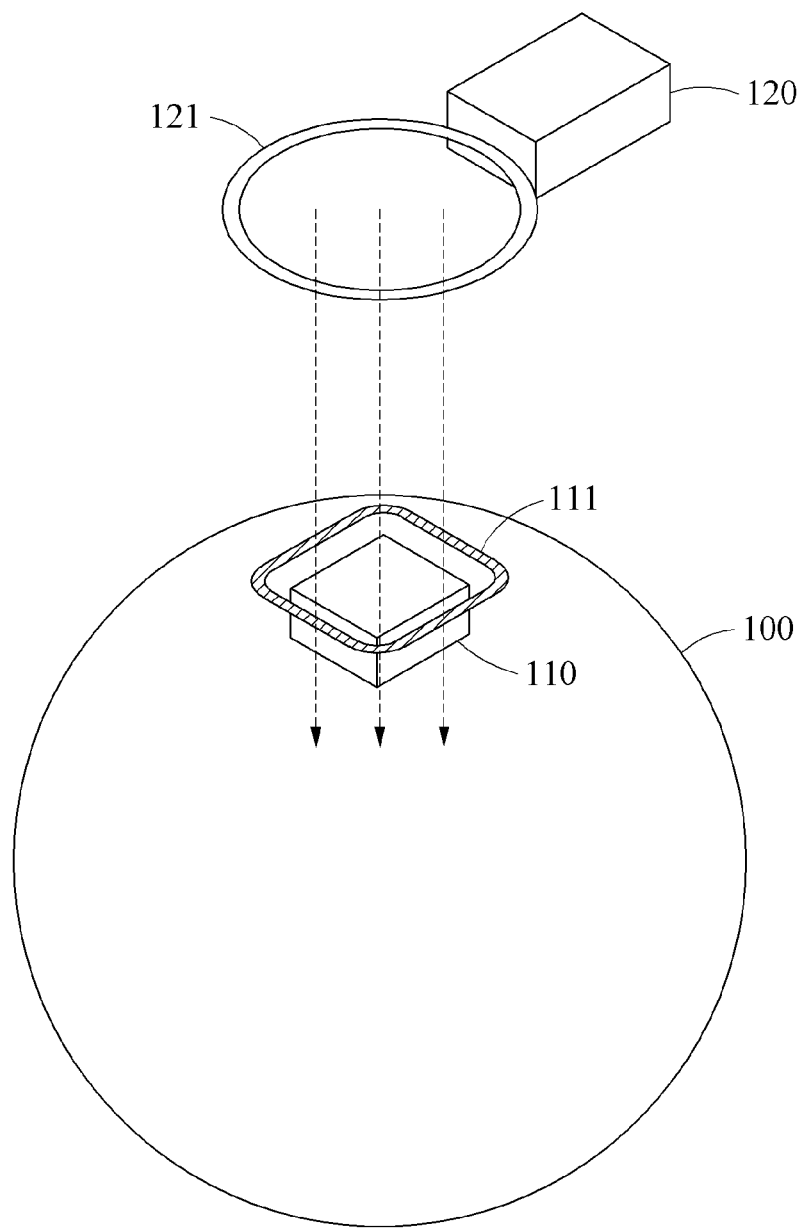
FIG. 1 illustrates an example in which an implantable apparatus wirelessly receives power.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Hereinafter, examples will be described in detail with reference to the accompanying drawings. The scope of the examples is not limited to the descriptions provided in the present specification. The examples are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

When describing the examples with reference to the accompanying drawings, like reference numerals refer to like constituent elements and a repeated description related thereto will be omitted. In the description of examples, detailed description of well-known related structures or functions will be omitted when it is deemed that such description will cause ambiguous interpretation of the present disclosure.

Also, the terms "first," "second," "A," "B," "(a)," "(b)," and the like may be used herein to describe components according to examples. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled, or joined to the second component.

A component having a common function with a component included in one example is described using a like name in another example. Unless otherwise described, description made in one example may be applicable to another example and detailed description within a duplicate range is omitted.

FIG. 1 illustrates an example in which an implantable apparatus wirelessly receives power.

In an example, the implantable apparatus may be inserted into a human body 100 and may interact with the human body 100. The implantable apparatus may detect a state of the human body 100. The implantable apparatus may communicate with an external device. The implantable apparatus may wirelessly receive power from an external wireless power transmitter.

The implantable apparatus may operate in a state of being inserted into the human body 100. The implantable apparatus may be applicable to, for example, a brain stimulator, a sleep apnea treatment device for sensing or stimulating lingual nervus, a deep brain neurostimulator (DBS), cochlear implants, an implantable cardiac defibrillator (ICD), an insulin pump, a muscle stimulant, or an artificial pancreas. However, these are merely examples, and a wireless power receiver may be applied to various types of implantable devices, without deviating from the sprit or scope of the illustrated examples described. The wireless power receiver may also be applied to an electronic device requiring a relatively small volume, in addition to implantable devices.

The implantable apparatus may have an electrode structure to communicate with an external device. Also, the implantable apparatus may include an antenna to wirelessly receive power from an external wireless power transmitter. The antenna may be referred to as a "reception coil". Since the implantable apparatus is inserted into a human body, a volume of the implantable apparatus needs to be small. An amount of current for electric stimulation and received power may be proportional to a size of an electrode and a size of the reception coil, respectively. Thus, effective space arrangement of the electrode and the reception coil may be needed.

In an example, the implantable apparatus may have an antenna structure that encloses a conductor case configured to protect internal components. An antenna may have a loop shape or a helical shape. Due to the antenna structure enclosing the conductor case, the antenna may be miniatured, and a transmission efficiency may be maximized. The size and the transmission efficiency of the antenna may be selectively adjusted. The antenna may have a shape of a loop wound at least once, and may be implemented by, for example, a wire or a flexible printed circuit board (PCB).

Referring to FIG. 1, the implantable apparatus may include a main body 110, and an antenna 111. The main body 110 may include an electrode and a processor. In an example, the antenna 111 may be shaped to enclose the main body 110. The implantable apparatus may wirelessly receive power from a wireless power transmitter. The implantable apparatus may wirelessly receive power via the antenna 111 from the wireless power transmitter.

The wireless power transmitter may include a main body 120 and an antenna 121. The wireless power transmitter may wirelessly transmit power using a resonance phenomenon between the antenna 121 having a shape of a coil and the antenna 111.

In an example, the main body 110 may be protected by a conductor case, and reception performance of the antenna 111 may be reduced by a surface current of the conductor case. The implantable apparatus may include ferrite disposed between a conductor case and the antenna 111. The ferrite may reduce an influence by the surface current of the conductor case. Thus, the implantable apparatus may further increase power reception performance.

Although the conductor case is insulated from the antenna, a circuit included in the conductor case may need to be electrically connected to the antenna. For example, the implantable apparatus may include a feed-through. The feed-through may include a conductive wire covered with an insulator. An insulator portion of the feed-through may be fastened into a hole, and the conductive wire of the feed-through may be connected to the antenna 111 and the circuit included in the conductor case. For example, the circuit in the conductor case may include a wireless power receiver.

The antenna 111, the electrode and the conductor case may be fixed by a molding structure of the insulator. In the molding structure, the antenna 111 may be fixed to an outside of the conductor case. The molding structure may be formed of an epoxy material and may be mechanically coupled to a protruding portion of the conductor case. For example, the protruding portion of the conductor case may have a shape of a hook, and a portion corresponding to the molding structure may have a groove into which a hook may be fixed. In the following description, the molding structure may be referred to as an "insulator case".

Figure 2A:
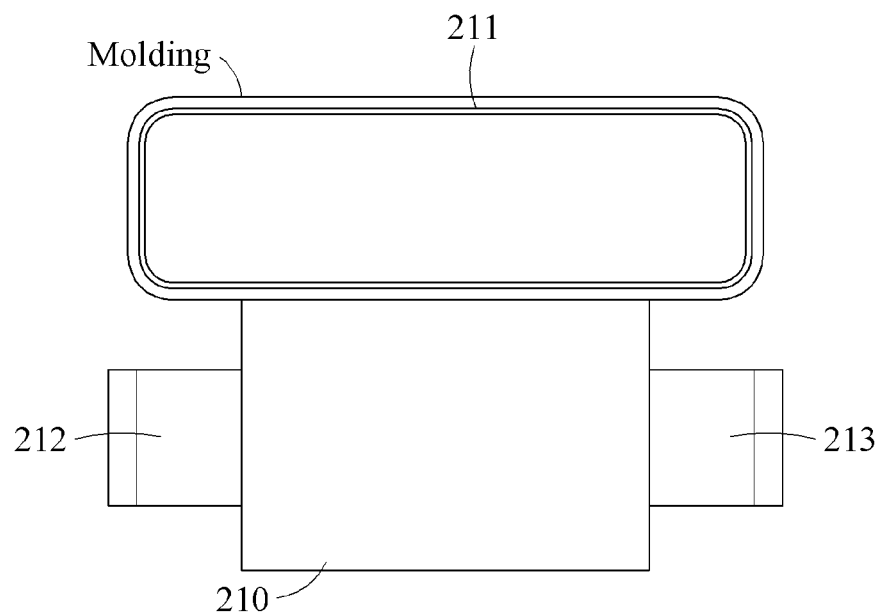
FIGS. 2A and 2B are diagrams illustrating a conventional implantable apparatus, respectively.
Figure 2B:
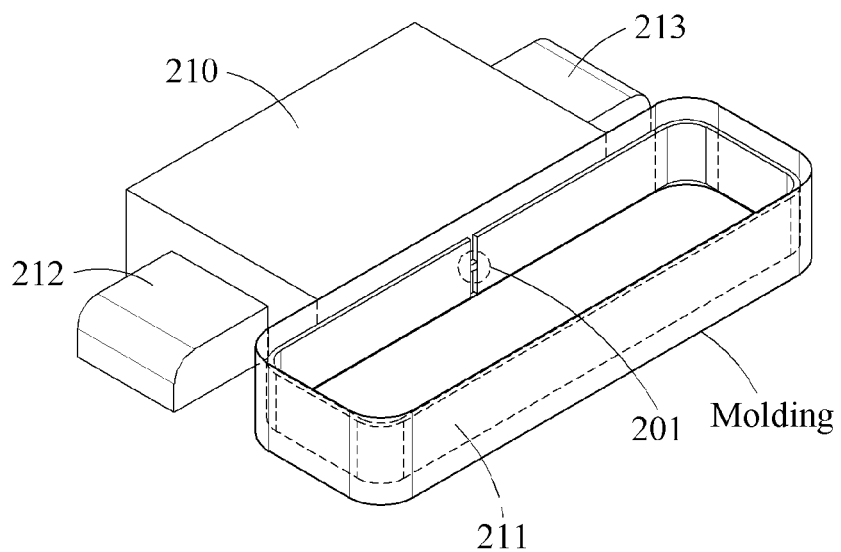

FIGS. 2A and 2B are conventional diagram illustrating an implantable apparatus.

Referring to FIG. 2A, the conventional implantable apparatus include a conductor case 210, a first electrode 212, a second electrode 213, and an antenna 211. The conductor case 210 may include a circuit configured to wirelessly receive power and to transmit and receive an electrode signal.

In FIG. 2A, the first electrode 212 and the second electrode 213 may be disposed on a left side and a right side of the conductor case 210, respectively. The first electrode 212 and the second electrode 213 may be connected to an electrode signal transceiver included in the conductor case 210. The antenna 211 may be disposed on another side of the conductor case 210.

Since the antenna 211 needs to be disposed on one side surface of the conductor case 210 and the antenna 211 and the conductor case 210 need to be electrically insulated, a connection between the antenna 211 and the conductor case 210 may lack robustness. Referring to FIG. 2B, the antenna 211 may be connected via two conductive wires 201 to a wireless power transceiver included in the conductor case 210. Since the conductor case 210 and the antenna 211 are insulated, the conductor case 210 and the antenna 211 may be spaced apart from each other. Since the conductor case 210 and the antenna 211 are physically connected by conductive wires only, robustness may be insufficient.

Referring to FIG. 2A, the antenna 211 may be disposed in a region separated from the conductor case 210. An inner region of the antenna 211 may be used to perform a function of receiving power from a wireless power transmitter. However, in an arrangement of the conductor case 210, the first electrode 212 and the second electrode 213, four corner regions may not be used to perform a function, and thus a space may be wasted.

Figure 3A:
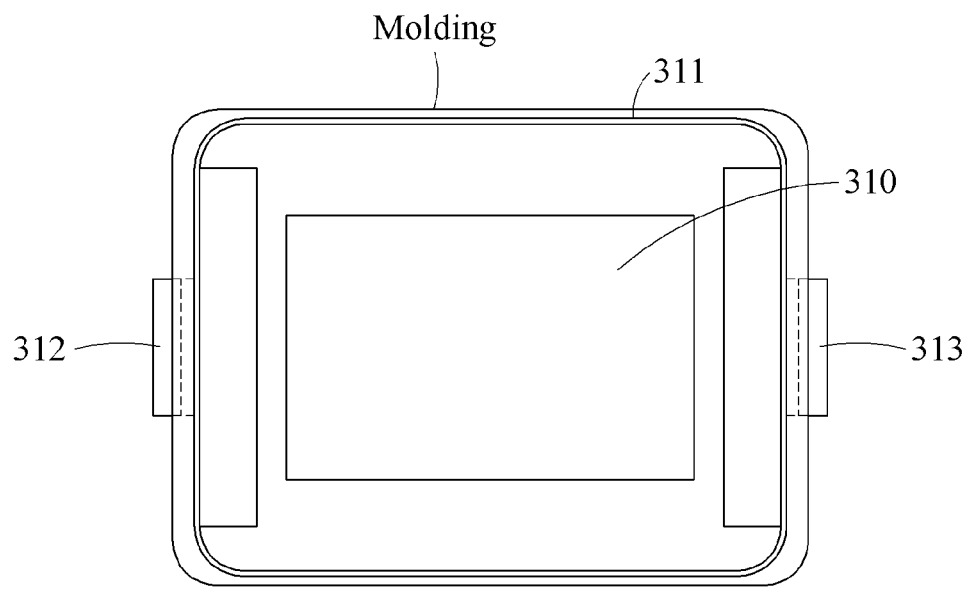
FIGS. 3A and 3B are diagrams illustrating an example of an implantable apparatus.
Figure 3B:
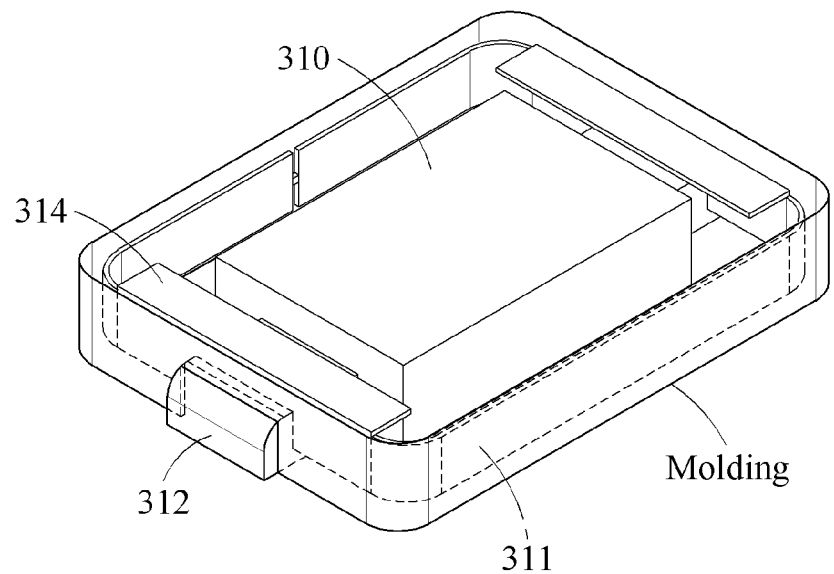
Figure 3C:
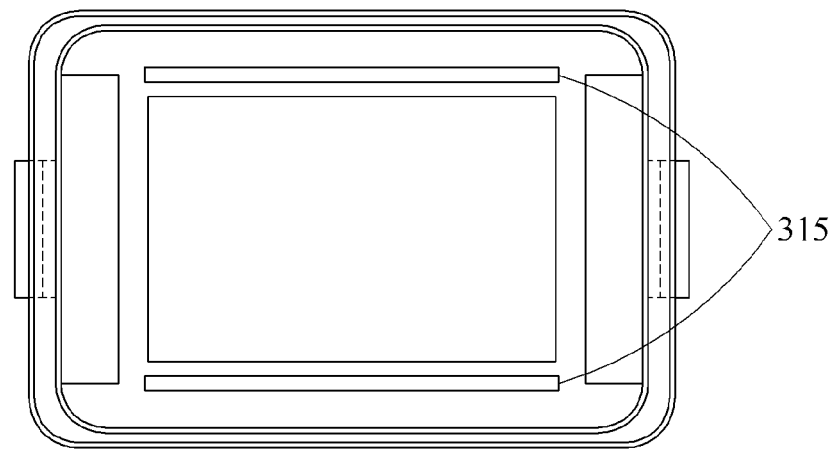
FIGS. 3C and 3D are diagrams illustrating an example of a structure in which ferrite is included in an implantable apparatus.
Figure 3D:
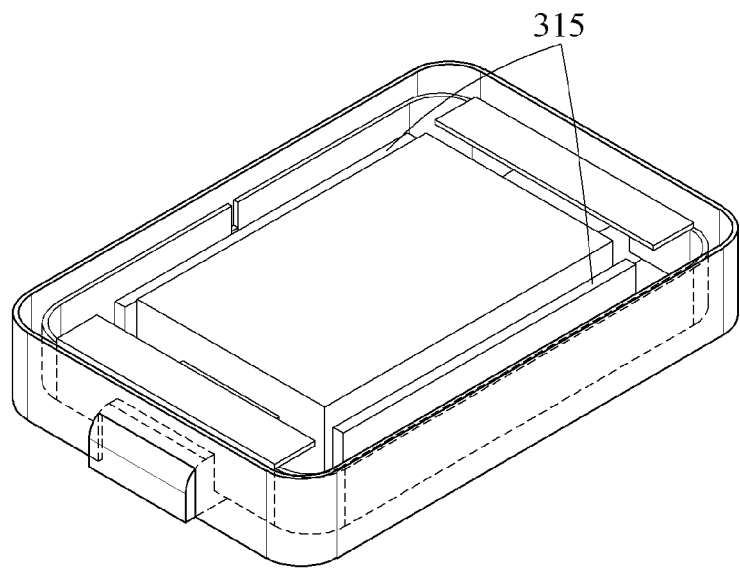
Figure 3E:
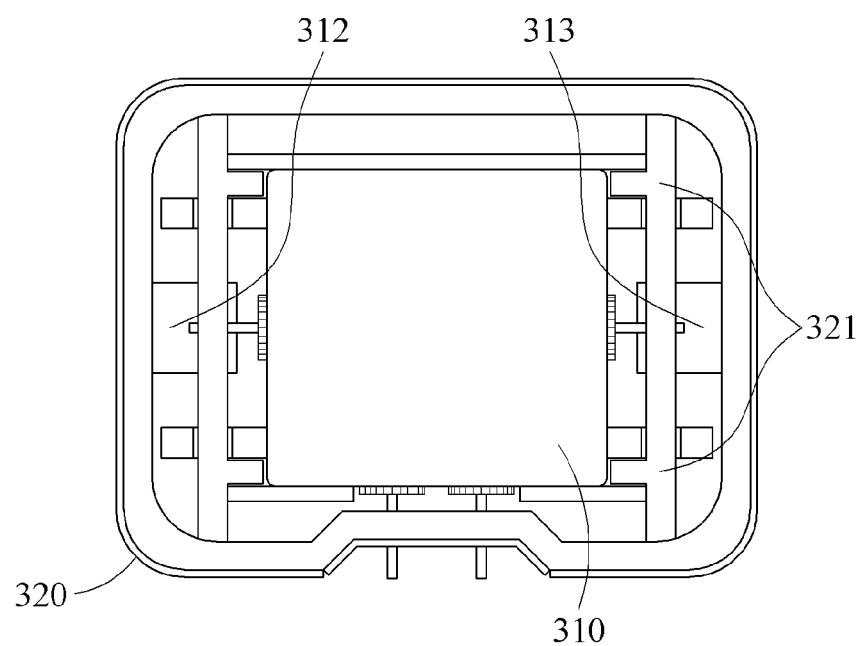
FIG. 3E is a diagram illustrating an example of a structure in which an insulating case is included in an implantable apparatus.

FIGS. 3A and 3B are diagrams illustrating an example of an implantable apparatus. FIGS. 3C and 3D are diagrams illustrating an example of a structure in which ferrite is included in the implantable apparatus. FIG. 3E is a diagram illustrating an example of a structure in which an insulating case is included in the implantable apparatus.

Referring to FIGS. 3A and 3B, the implantable apparatus may include a conductor case 310, a first electrode 312, a second electrode 313, and an antenna 311. The conductor case 310 may include a circuit configured to wirelessly receive power and to transmit and receive an electrode signal.

In FIGS. 3A and 3B, the first electrode 312 and the second electrode 313 may be disposed on a left side and a right side of the conductor case 310, respectively. The first electrode 312 and the second electrode 313 may be connected to an electrode signal transceiver included in the conductor case 310. The antenna 311 may be connected to a wireless power receiver included in the conductor case 310. The conductor case 310 may protect the wireless power receiver and the electrode signal transceiver.

Although the conductor case 310 is insulated from the antenna 311, the circuit included in the conductor case 310 may be electrically connected to the antenna 311. In an example, the implantable apparatus may include a feed-through. The antenna 311 may be connected via the feed-through to the wireless power receiver, and may be electrically insulated from the conductor case 310. The feed-through may include a conductive wire covered with an insulator. An insulator portion of the feed-through may be fastened into a hole, and the conductive wire of the feed-through may be connected to the antenna 311 and the circuit included in the conductor case 310. For example, the circuit in the conductor case 310 may include the wireless power receiver.

The antenna 311 may be disposed to enclose the conductor case 310. The antenna 311 may enclose the conductor case 310, and a portion 314 of the antenna 311 may be disposed above each of the first electrode 312 and the second electrode 313. The antenna 311 may have a height greater than or equal to a threshold. The antenna 311 may vertically enclose the conductor case 310 and may be horizontally disposed above a protruding portion of each of the first electrode 312 and the second electrode 313.

The antenna 311 may have a structure of enclosing the conductor case 310 and may be physically fixed to the first electrode 312 and the second electrode 313. The antenna 311 may be connected via two conductive wires to a wireless power transceiver included in the conductor case 310. Since the conductor case 310 and the antenna 311 are insulated, the conductor case 310 and the antenna 311 may be spaced apart from each other. The antenna 311 of the implantable apparatus may enclose the conductor case 310 and may be physically fixed to the first electrode 312 and the second electrode 313, and accordingly robustness of a connection relationship may be greater than that of FIG. 2A.

Referring to FIG. 3A, the antenna 311 may be disposed to enclose the conductor case 310. An inner region of the antenna 311 may be used to perform a function of receiving power from a wireless power transmitter. In an arrangement of the conductor case 310, the first electrode 312 and the second electrode 313, all four corner regions may be included in the inner region of the antenna 311, and thus a waste of space may be minimized. In comparison to FIGS. 2A and 2B, the inner region of the antenna 311 may be effectively used to reduce a volume of the implantable apparatus, and to increase a wireless power transmission efficiency.

In an example, the antenna 311 may be a ribbon-type antenna shared for wireless power transmission (WPT) and/or near field communication (NFC). The conductor case 310 may have a size of 11×10.2×4 millimeters (mm). The antenna 311 may have a size of 21.8×17.4×3.2 mm. An insulator case may have a size of 23.2×18.4×4 mm. In this example, a transmission efficiency of wireless power transmission and reception of the implantable apparatus may be 20% @ 3 centimeter (cm), and the implantable apparatus may perform an NFC with a frequency of 13.56 megahertz (MHz) at a communication distance of 3 cm.

In another example, the antenna 311 may be a ribbon-type antenna shared for WPT and/or medical implanted communication system (MICS). The conductor case 310 may have a size of 10×4×2 mm. The antenna 311 may have a size of 12×6×2 mm. In this example, a transmission efficiency of wireless power transmission and reception of the implantable apparatus may be 0.5% @ 1 cm at a frequency of 13.56 MHz, and the implantable apparatus may perform a MICS communication with a frequency of 400 MHz at a communication distance of 1.5 meters (m).

Reception performance of the antenna 311 may be reduced by a surface current of the conductor case 310. Referring to FIGS. 3C and 3D, the implantable apparatus may include ferrite 315 disposed between the conductor case 310 and the antenna 311. The ferrite 315 may reduce an influence by the surface current of the conductor case 310. Thus, the implantable apparatus may further increase power reception performance.

Referring to FIG. 3E, the implantable apparatus may further include an insulator case 320. The antenna 311, the first electrode 312, the second electrode 313 and the conductor case 310 may be fixed by the insulator case 320. The insulator case 320 may fix the antenna 111 to the outside of the conductor case 310. The insulator case 320 may be formed of an epoxy material and may be mechanically coupled to a protruding portion of the conductor case 310. For example, the protruding portion of the conductor case 310 may have a shape of a hook, and a portion corresponding to the insulator case 320 may include a support 321 including a groove into which a hook may be fixed.

Figure 4A:
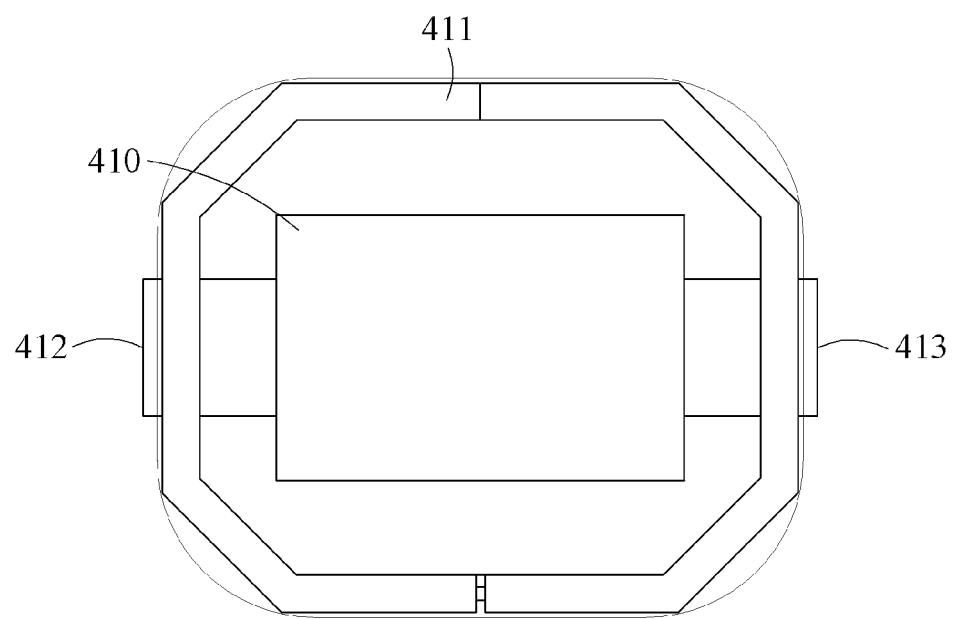
FIGS. 4A and 4B are diagram illustrating another example of an implantable apparatus.
Figure 4B:
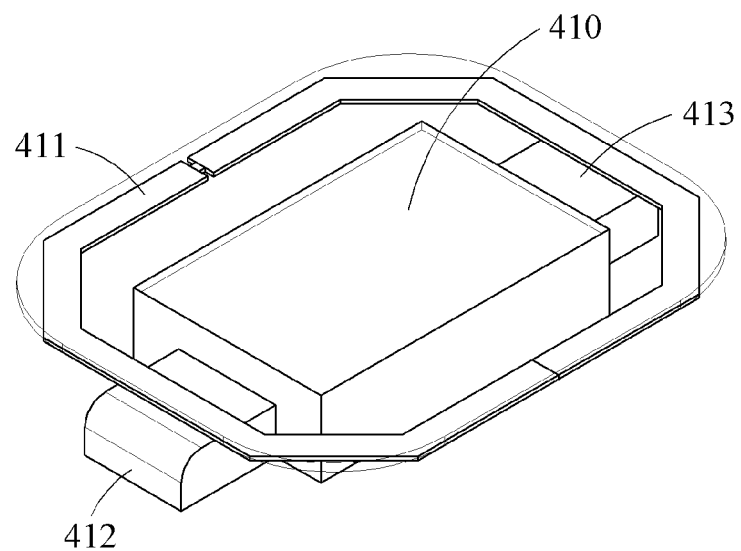
Figure 4C:
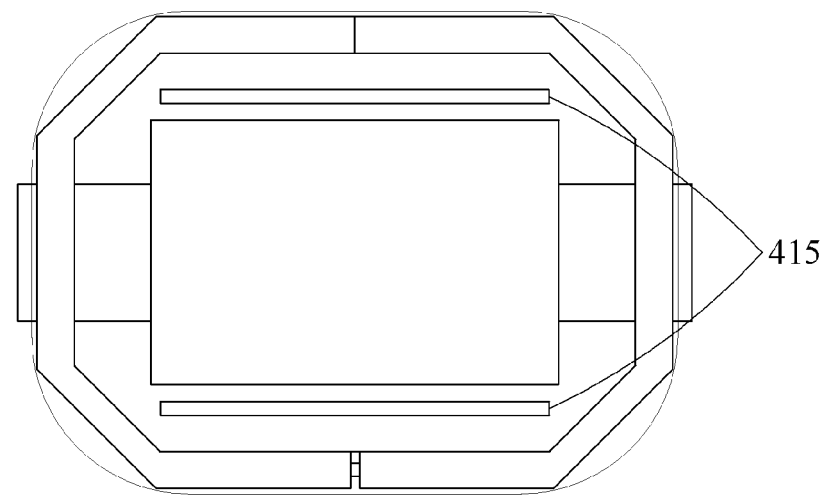
FIGS. 4C and 4D are diagrams illustrating another example of a structure in which ferrite is included in an implantable apparatus.
Figure 4D:
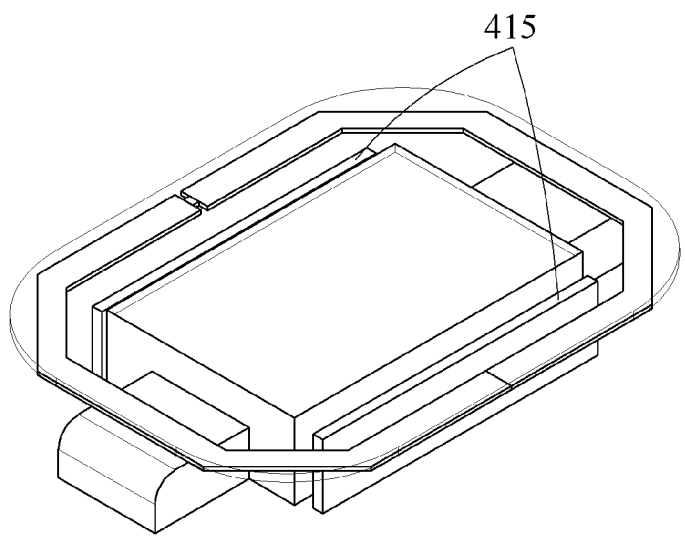

FIGS. 4A and 4B are diagrams illustrating another example of an implantable apparatus. FIGS. 4C and 4D are diagrams illustrating another example of a structure in which ferrite is included in the implantable apparatus, respectively.

In FIGS. 4A and 4B, a first electrode 412 and a second electrode 413 may be disposed on a left side and a right side of a conductor case 410, respectively. The first electrode 412 and the second electrode 413 may be connected to an electrode signal transceiver included in the conductor case 410. The antenna 411 may be connected to a wireless power receiver included in the conductor case 410. The conductor case 410 may protect the wireless power receiver and the electrode signal transceiver.

Although the conductor case 410 is insulated from the antenna 411, a circuit included in the conductor case 410 may need to be electrically connected to the antenna 411. For example, the implantable apparatus may include a feed-through. The antenna 411 may be connected via the feed-through to the wireless power receiver, and may be electrically insulated from the conductor case 410. The feed-through may include a conductive wire covered with an insulator. An insulator portion of the feed-through may be fastened into a hole, and the conductive wire of the feed-through may be connected to the antenna 411 and the circuit included in the conductor case 410. For example, the circuit in the conductor case 410 may include the wireless power receiver.

The antenna 411 may be spaced apart from the conductor case 410 above the conductor case 410, and may be disposed to enclose the conductor case 410. A plane in which the antenna 411 is disposed may be at the same level as or at a higher level than a top surface of the conductor case 410. The antenna 411 may have a structure in which a conductive wire with a width greater than or equal to a threshold is disposed on a PCB.

The antenna 411 may be connected via two conductive wires to a wireless power transceiver included in the conductor case 410, and may be spaced apart from the conductor case 410 to be insulated from the conductor case 410. The antenna 411 of the implantable apparatus may be disposed above the conductor case 410 and may be physically fixed to the conductor case 410, and thus robustness of a connection relationship may be greater than that of FIG. 2A.

Referring to FIG. 4A, the antenna 411 may be disposed to enclose the conductor case 410. An inner region of the antenna 411 may be used to perform a function of receiving power from a wireless power transmitter. In an arrangement of the conductor case 410, the first electrode 412 and the second electrode 413, all four corner regions may be included in the inner region of the antenna 411, and thus a waste of space may be minimized. In comparison to FIGS. 2A and 2B, the inner region of the antenna 411 may be effectively used to reduce a volume of the implantable apparatus, and to increase a wireless power transmission efficiency.

Reception performance of the antenna 411 may be reduced by a surface current of the conductor case 410. Referring to FIGS. 4C and 4D, the implantable apparatus may include ferrite 415 disposed between the conductor case 410 and the antenna 411. The ferrite 415 may reduce an influence by the surface current of the conductor case 410. Thus, the implantable apparatus may further increase power reception performance.

Figure 5:
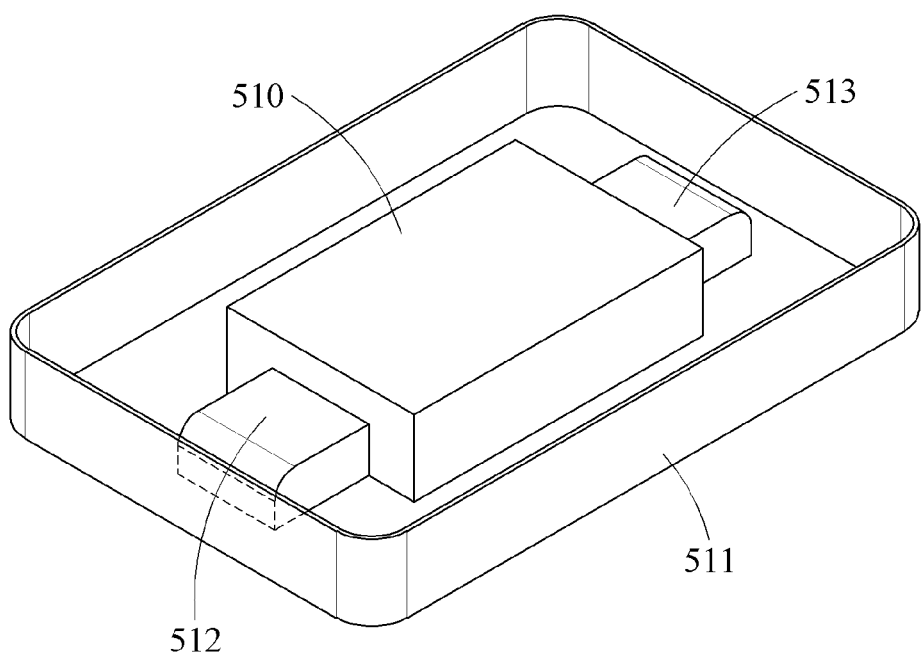
FIG. 5 is a diagram illustrating another example of an implantable apparatus.

FIG. 5 is a diagram illustrating another example of an implantable apparatus.

In FIG. 5 a first electrode 512 and a second electrode 513 may be disposed on a left side and a right side of a conductor case 510, respectively. The first electrode 512 and the second electrode 513 may be connected to an electrode signal transceiver included in the conductor case 510. The antenna 511 may be connected to a wireless power receiver included in the conductor case 510. The conductor case 510 may protect the wireless power receiver and the electrode signal transceiver.

Although the conductor case 510 is insulated from the antenna 511, a circuit included in the conductor case 510 may need to be electrically connected to the antenna 511. For example, the implantable apparatus may include a feed-through. The antenna 511 may be connected via the feed-through to the wireless power receiver, and may be electrically insulated from the conductor case 510. The feed-through may include a conductive wire covered with an insulator. An insulator portion of the feed-through may be fastened into a hole, and the conductive wire of the feed-through may be connected to the antenna 511 and the circuit included in the conductor case 510. For example, the circuit in the conductor case 510 may include the wireless power receiver.

The antenna 511 may be disposed to enclose all the first electrode 512, the second electrode 513 and the conductor case 510. As shown in FIG. 5, the first electrode 512 and the second electrode 513 may not protrude outward from the antenna 511. The antenna 511 may have a height greater than or equal to a threshold.

For example, the implantable apparatus may include a feed-through. The antenna 511 may be connected via the feed-through to the wireless power receiver, and may be electrically insulated from the conductor case 510. The feed-through may include a conductive wire covered with an insulator. An insulator portion of the feed-through may be fastened into a hole, and the conductive wire of the feed-through may be connected to the antenna 511 and the circuit included in the conductor case 510. For example, the circuit in the conductor case 510 may include the wireless power receiver.

The implantable apparatus may include ferrite 515 disposed between the conductor case 510 and the antenna 511. The ferrite 515 may reduce an influence by a surface current of the conductor case 510. Thus, the implantable apparatus may further increase power reception performance.

Figure 6:
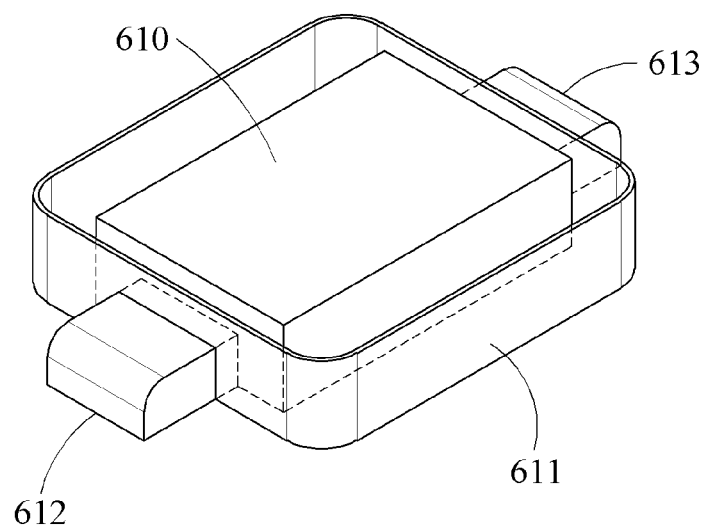
FIG. 6 is a diagram illustrating another example of an implantable apparatus.

FIG. 6 is a diagram illustrating another example of an implantable apparatus.

In FIG. 6 a first electrode 612 and a second electrode 613 may be disposed on a left side and a right side of a conductor case 610, respectively. The first electrode 612 and the second electrode 613 may be connected to an electrode signal transceiver included in the conductor case 610. The antenna 611 may be connected to a wireless power receiver included in the conductor case 610. The conductor case 610 may protect the wireless power receiver and the electrode signal transceiver.

Although the conductor case 610 is insulated from the antenna 611, a circuit included in the conductor case 610 may need to be electrically connected to the antenna 611. For example, the implantable apparatus may include a feed-through. The antenna 611 may be connected via the feed-through to the wireless power receiver, and may be electrically insulated from the conductor case 610. The feed-through may include a conductive wire covered with an insulator. An insulator portion of the feed-through may be fastened into a hole, and the conductive wire of the feed-through may be connected to the antenna 611 and the circuit included in the conductor case 610. For example, the circuit in the conductor case 610 may include the wireless power receiver.

The antenna 611 may enclose the conductor case 610. The first electrode 612 and the second electrode 613 may protrude outward from the antenna 611. In an example, the antenna 611 may be disposed at a higher level than each of the first electrode 612 and the second electrode 613.

The implantable apparatus may include a feed-through. The antenna 611 may be connected via the feed-through to the wireless power receiver, and may be electrically insulated from the conductor case 610. The feed-through may include a conductive wire covered with an insulator. An insulator portion of the feed-through may be fastened into a hole, and the conductive wire of the feed-through may be connected to the antenna 611 and the circuit included in the conductor case 610.

The implantable apparatus may include ferrite 615 disposed between the conductor case 610 and the antenna 611. The ferrite 615 may reduce an influence by a surface current of the conductor case 610. Thus, the implantable apparatus may further increase power reception performance.

While this disclosure includes specific examples, it will be apparent after an understanding of the present disclosure that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An implantable apparatus, comprising:
a first electrode;
a second electrode;
an electrode signal transceiver connected to the first electrode and the second electrode;
an antenna, the antenna comprising a flat conductive wire provided on a printed circuit board (PCB);
a wireless power receiver connected to the antenna; and
a conductor case comprising major surfaces having a largest surface area among plural surface areas of the conductor case, the major surfaces including a top surface and a bottom surface, the bottom surface being provided below the top surface respective to an orientation of the conductor case and the antenna, the conductor case being configured to protect the electrode signal transceiver and the wireless power receiver, wherein the flat conductive wire is configured to enclose an outer perimeter of the top surface of the conductor case, the flat conductive wire traversing in a first direction and a second direction longitudinally along each respective lateral side surface of the top surface of the conductor case, and wherein the flat conductive wire forms an antenna plane being at same height or a greater height above the top surface, respective to the bottom surface, as a top plane defined by the top surface of the conductor case.

2. The implantable apparatus of claim 1, further comprising:
ferrite disposed between the conductor case and the antenna.

3. The implantable apparatus of claim 1, wherein
the antenna is connected via a feed-through to the wireless power receiver, and
the antenna is electrically insulated from the conductor case.

4. The implantable apparatus of claim 3, wherein the feed-through comprises a conductive wire covered with an insulator.

5. The implantable apparatus of claim 4, wherein the insulator is fastened in a hole, and the conductive wire is connected to the antenna and a circuit in the conductor case.

6. The implantable apparatus of claim 1, further comprising:
an insulator case configured to protect the first electrode, the second electrode, the antenna, and the conductor case,
wherein the insulator case is configured to fix the first electrode, the second electrode and a protruding portion of the conductor case.

7. The implantable apparatus of claim 1, wherein the antenna is disposed at a higher height than each of the first electrode and the second electrode, and the first electrode and the second electrode protrude outward from the antenna.

8. The implantable apparatus of claim 7, further comprising:
ferrite disposed between the conductor case and the antenna.

9. The implantable apparatus of claim 7, wherein:
the antenna is connected via a feed-through to the wireless power receiver, and
the antenna is electrically insulated from the conductor case.

10. The implantable apparatus of claim 7, further comprising:
an insulator case configured to protect the first electrode, the second electrode, the antenna, and the conductor case,
wherein the insulator case is configured to fix the first electrode, the second electrode and a protruding portion of the conductor case.

11. The implantable apparatus of claim 1, wherein a portion of the antenna is disposed above each of the first electrode and the second electrode.

12. The implantable apparatus of claim 11, further comprising:
ferrite disposed between the conductor case and the antenna.

13. The implantable apparatus of claim 11, wherein
the antenna is connected via a feed-through to the wireless power receiver, and
the antenna is electrically insulated from the conductor case.

14. The implantable apparatus of claim 11, further comprising:
an insulator case configured to protect the first electrode, the second electrode, the antenna, and the conductor case,
wherein the insulator case is configured to fix the first electrode, the second electrode and a protruding portion of the conductor case.

15. The implantable apparatus of claim 1, wherein the antenna is further configured to enclose the first electrode and the second electrode, and the first electrode and the second electrode do not protrude outward from the antenna.

16. The implantable apparatus of claim 15, further comprising:
ferrite disposed between the conductor case and the antenna.

17. The implantable apparatus of claim 15, wherein
the antenna is connected via a feed-through to the wireless power receiver, and
the antenna is electrically insulated from the conductor case.

18. The implantable apparatus of claim 15, further comprising:
an insulator case configured to protect the first electrode, the second electrode, the antenna, and the conductor case,
wherein the insulator case is configured to fix the first electrode, the second electrode and a protruding portion of the conductor case.

19. The implantable apparatus of claim 1, wherein an entirety of the flat conductive wire is disposed in the antenna plane that is parallel with the top plane of the top surface.

20. The implantable apparatus of claim 19, wherein the PCB is orientated parallel to the antenna plane and the top plane.

21. The implantable apparatus of claim 1, wherein the top surface of the conductor case defines a rectangle shape including width sides, length sides, and curved corner sides connecting respective width sides and length sides, and
wherein the flat conductive wire follows the width sides, the length sides, and the curved corner sides to stay within an area of the top surface.

* * * * *